March 12, 1963 G. MERRILL Plant Pat. 2,239
PEACH TREE
Filed Dec. 12, 1961
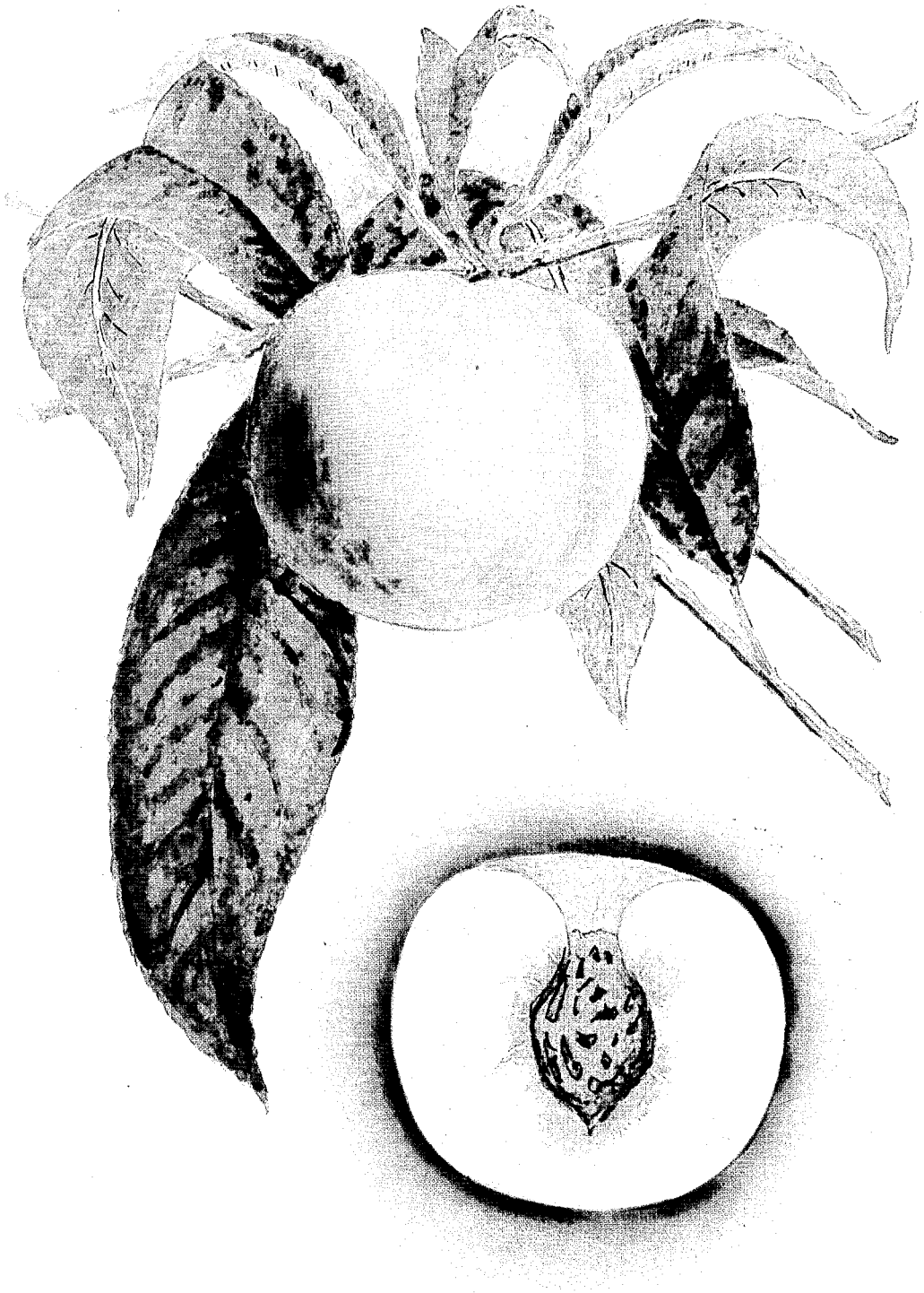
WITNESS
Addison E. Avery
INVENTOR
GRANT MERRILL
HUEBNER & WORREL
ATTORNEYS
BY Richard M. Worrel United States Patent Office Plant Pat. 2,239
Patented Mar. 12, 1963

2,239
PEACH TREE

Grant Merrill, P.O. Box 392, Red Bluff, Calif.

Filed Dec. 12, 1961, Ser. No. 158,918
1 Claim. (Cl. 47—62)

This invention relates to a new and distinct variety of peach tree broadly characterized by its ability to bear freestone peaches of good shipping quality which have a yellow flesh of exceptional firmness and a skin of vivid red color.

Further characteristics of the new variety are that it ripens five to ten days earlier than Elberta (unpatented) and blossoms following medium chilling requirements. The present variety most nearly resembles Merrill Gem-free of United States Plant Patent No. 1,409, but is an improvement thereover in that the fruit of the new variety ripens forty to forty-five days later, the flesh thereof is more nearly free of the stone and the skin is of a brighter red color.

I originated the present variety of peach tree on my farm, near Red Bluff, Tehama County, California in the following manner: A J. H. Hale (unpatented) peach tree was crossed with Flaming Gold (unpatented) nectarine tree. The resulting seeds were planted and grown to maturity. Open pollinated blossoms of the resultant trees produced seeds which in turn were germinated and grown. One of the seedlings resulted in a mid-season nectarine known in our seedling block as C18–20. Seeds from this seedling were planted and from those grew the subject peach tree which was given the seedling number L–152. Expressed in formula the peach tree is represented, as follows: ((J. H. Hale × Flaming Gold) Open) Open.

Observations on the fruit of L–152 were made in July of 1956. A group of newly planted mixed varieties were budded in August of that year to this new variety on my farm near Red Bluff, California. The resulting growth fruited in July 1958, and the fruit and tree characteristics precisely resembled the original tree.

In the drawing, the upper drawing is a water color painting showing a characteristic fruit bearing twig of the subject peach tree having leaves and a mature peach thereon. The lower drawing is a water color painting showing the characteristic fruit of the subject peach tree divided on its suture plane to reveal flesh coloration and showing a pit in place therein.

Referring more specifically to the pomological characteristics of this new and distinct variety of peach tree, the following is an outline description thereof, all major color plate identifications being by reference to Maerz and Paul Dictionary of Color:

*Tree*

Shape: Medium size, medium vigor, medium spreading and dense, vase formed by pruning, productive, regular bearer, hardiness unknown.

Trunk: Medium stocky, medium shaggy, grey in color.

Branches: Older branches, medium shaggy, grey; younger branches, moderately smooth and brown. Lenticels—medium size, medium large.

Leaves (Selected from midportion of vigorous unbranched terminal shoots 18" to 24" long):

*Length.*—6" to 7½", average 6 11/16".

*Width.*—1½" to 2", average 1 11/16".

*Form.*—Medium size, lanceloate, tip acuminate, medium thick.

*Color.*—Upper surface, medium green (22–L–5) to (22–L–7) plus yellow. Underside, lighter green (21–K–6). Midrib, lighter yellowish green (9–J–1).

*Class* (Meader and Blake: Proc. Am. Soc. Hort. Sci., vol. 37, page 206).—2 to 3. Width-length ratio—.25. Apex angle (1" from tip)—37° to 40°, average 38°. Base angle (½" from petiole)— 85° to 98°, average 90°.

*Margin.*—Crenate.

*Petiole.*—Medium long, medium slender.

*Glands.*—Usually two to four, average three. Opposite and alternate, reniform, green to greenish yellow, usually on petiole, sometimes on the base of leaf.

*Stipules.*—At base of leaf, falling off early.

Flower buds: Hardiness unknown, medium size, truncate to obtuse, free pubescent.

Flowers: Mid-season, pink, abundant fertile pollen.

*Fruit*

Maturity when described, firm ripe to eating ripe.

Size: Variable.

*Axial diameter.*—2½" to 3", average 2 11/16".

*Transverse in suture plane.*—2⅝" to 3", average 2 13/16".

*At right angles to suture plane.*—2½" to 3", average 2 13/16".

Form: Globose to slightly compressed axially.

*Suture.*—Inconspicuous, extends from base to beyond but discontinuous at apex, has slight depression beyond pistil point.

*Ventral surface.*—Rounded, slightly lipped on one side.

*Cavity.*—Abrupt, elongated on suture plane with suture showing on both sides. Depth—½" to ¾", average 19/32". Breadth—7/16" to ⅝", average ½".

*Markings.*—Yellow, usually with some red blush, some with complete red blush.

*Base.*—Truncate to retuse.

*Apex.*—Rounded, pistil point apical, depressed to mucronate.

*Stem.*—Length ⅛" to ⅜", average ¼"; diameter about ⅛".

*Skin.*—Medium thick, medium tough to tough, free when soft ripe; no tendency to crack, golden yellow (9–L–5) to orange yellow (9–J–9) to deep rose (1–K–10) with bright red (3–K–6) to red brown (7–L–6) blush over half to nearly all of the surface.

*Down.*—Moderate, short, does not roll up when rubbed.

Flesh:

*Color.*—Whitish yellow (9–B–2) to yellow (9–L–5) to orange (9–L–9) with red (3–L–4) at pit. Some red throughout flesh when fully ripe.

*Amygdalin.*—Moderate.

*Juice.*—Moderately rich.

*Texture.*—Firm, fine, meaty.

*Fibers.*—Few, fine.

*Ripens.*—Evenly.

*Flavor.*—Mild, subacid.

*Aroma.*—Distinct.

*Eating quality.*—Good.

Stone: Free—adheres to flesh near base in some fruits, with long fibers.

*Size.*—Medium to small. Highly variable, especially in thickness. Length—1 5/16" to 1 9/16", average 1 7/16". Breadth—⅞" to 1 3/16", average 1".

*Thickness.*—9/16" to 15/16", average 11/16".

*Form.*—Obovate, tip acuminate and usually short, occasionally quite long.

*Base.*—Straight to slightly oblique.

*Hilum.*—Oval.

*Apex.*—Cuspidate, few stones quite long.

*Sides.*—Mostly equal, few unequal.

*Surface.*—Pitted throughout center, grooves on either side and toward base.

*Ventral edge.*—Many small grooves interrupted.

*Dorsal edge.*—Two ridges, occasionally partial third ridge, usually interrupted near the apex, occasionally elsewhere.

*Color.*—Tan, but usually stained reddish purple (7–E–6) plus red.

*Tendency to split.*—Little.

Use: Market, dessert, long distance shipping.

Keeping quality: Good.

Although the new variety of peach tree possesses the described characteristics under the growing conditions prevailing throughout most of the commercial peach producing areas in California, having been first observed near Red Bluff, Tehama County, California, at the northern end of the Sacramento Valley and later confirmed by observation of the same variety near the southern end of the San Joaquin Valley of California, approximately four hundred miles farther south, it is to be understood that variations of the usual magnitude in characteristics incident to growing conditions, fertilization, pruning, thinning and pest control are to be expected.

Having thus decribed my new peach tree, what I claim as new and desire to be secured by Letters Patent is:

A new and distinct variety of peach tree, substantially as illustrated and described, characterized by its bearing of exceptionally firm, yellow fleshed freestone fruit, the skin thereof having vivid red coloring, the fruit being of good shipping quality and ripening five to ten days earlier than the Elberta (unpatented), and further characterized by most nearly resembling Merrill Gemfree of United States Plant Patent No. 1,409 but being an improvement thereover by bearing fruit which has flesh more free from the stone, is of a brighter red in skin coloring, and which ripens forty to forty-five days later.

No references cited.